United States Patent [19]

Shionozaki et al.

[11] 4,279,771
[45] Jul. 21, 1981

[54] (2'-CYANO-4'-N-ALKYL)PHENYL-3-CHLORO-4-N-ALKOXY BENZOATES AND LIQUID CRYSTAL COMPOSITIONS THEREOF

[75] Inventors: Yoshio Shionozaki; Sakao Kanbe; Katsumori Takei, all of Suwa, Japan

[73] Assignee: Kabushiki Kaisha Suwa Seikosha, Tokyo, Japan

[21] Appl. No.: 114,775

[22] Filed: Jan. 23, 1980

[30] Foreign Application Priority Data

Jan. 26, 1979 [JP] Japan .................................. 54-8590
Apr. 4, 1979 [JP] Japan .................................. 54-40659
Oct. 26, 1979 [JP] Japan .................................. 54-138546

[51] Int. Cl.³ .................... C07C 121/75; C09K 3/34; G02F 1/13
[52] U.S. Cl. ...................... 252/299.63; 260/465 D; 350/350 R; 252/299.64; 252/299.65; 252/299.67
[58] Field of Search .............. 260/465 D; 252/299

[56] References Cited

U.S. PATENT DOCUMENTS

| 4,110,243 | 8/1978 | Albert-Mellah et al. ......... 252/299 |
| 4,195,916 | 4/1980 | Coates et al. .................. 252/299 X |
| 4,198,312 | 4/1980 | Sato et al. ..................... 252/299 |

FOREIGN PATENT DOCUMENTS 2836086  3/1979  Fed. Rep. of Germany .

Primary Examiner—Dolph H. Torrence
Attorney, Agent, or Firm—Blum, Kaplan, Friedman, Silberman & Beran

[57] ABSTRACT

A new ester compound suitable for use in a liquid crystal composition is provided. The compound is a (2'-cyano-4'-alkyl)phenyl-3-chloro-4 alkoxybenzoate represented by the following formula:

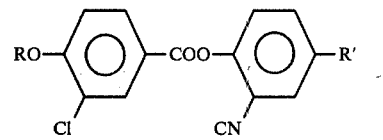

wherein R and R' are selected from straight-chain alkyl groups having from one to eight carbon atoms. The ester is not a liquid crystal compound, but upon addition to a liquid crystal composition increases the absolute value of the dielectric anisotropy in the high frequency range. Such compositions are particularly well suited for the two frequency matrix-addressing drive in a liquid crystal display for complex character and graphic displays. The esters are prepared by condensing an acid chloride having the general formula

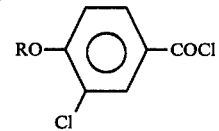

and a phenol having the general formula

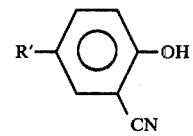

wherein R and R' are as defined above.

21 Claims, 17 Drawing Figures 3-chloro-4-hydroxybenzoic acid 3-chloro-4-n-propyloxybenzoic acid 3-chloro-4-n-propyloxybenzoyl chloride 2-cyano-4-pentylphenol

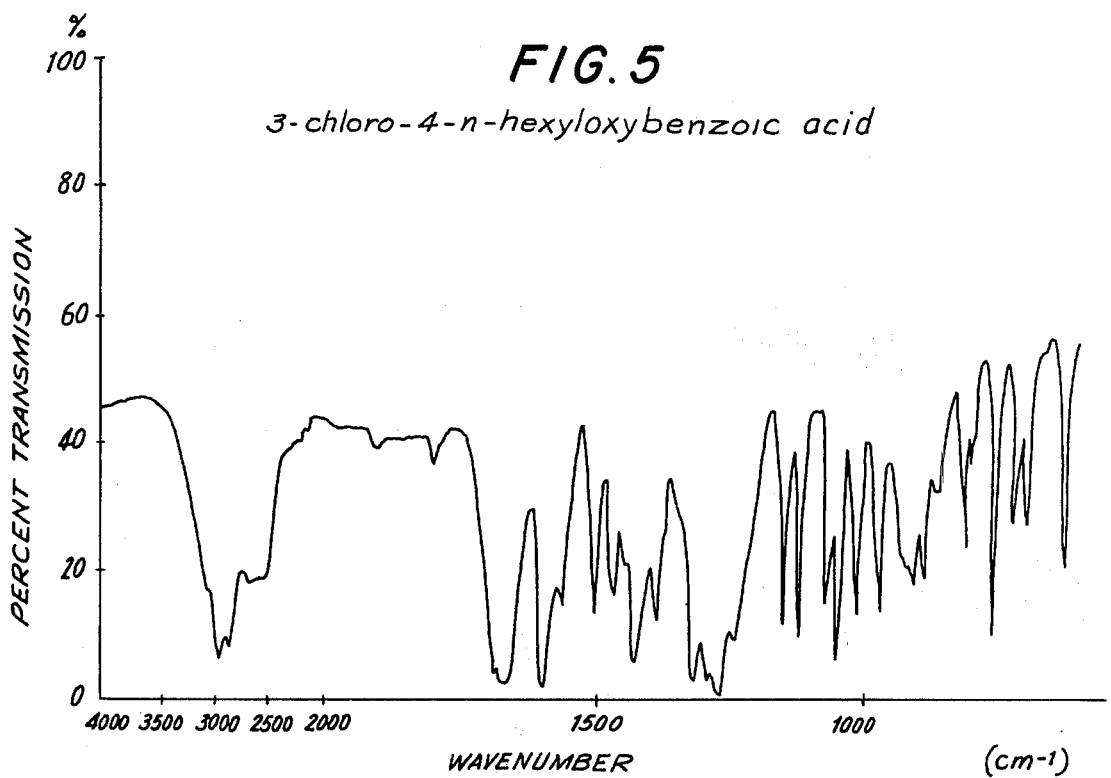
FIG.5 3-chloro-4-n-hexyloxybenzoic acid
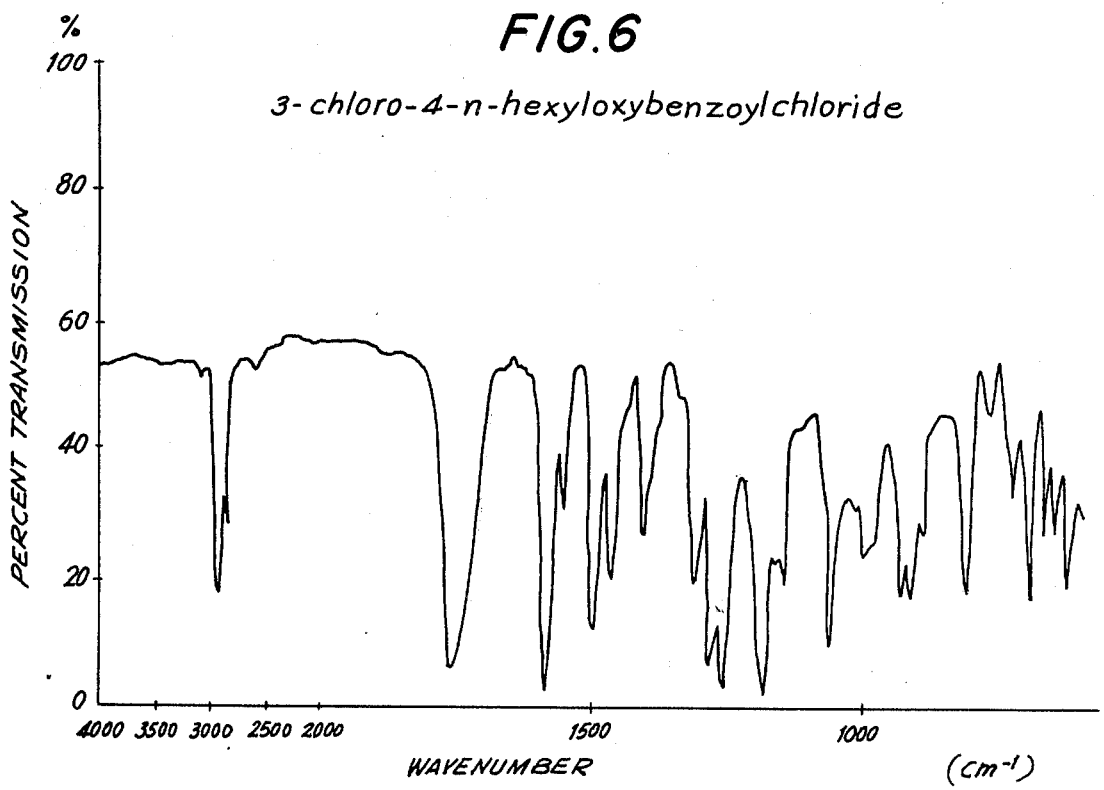
FIG.6 3-chloro-4-n-hexyloxybenzoyl chloride (2'-cyano-4'-n-pentyl)phenyl-3-chloro-4-n-propyloxybenzoate (2'-cyano-4'-n-propyl)phenyl-3-chloro-4-n-heptyloxybenzoate

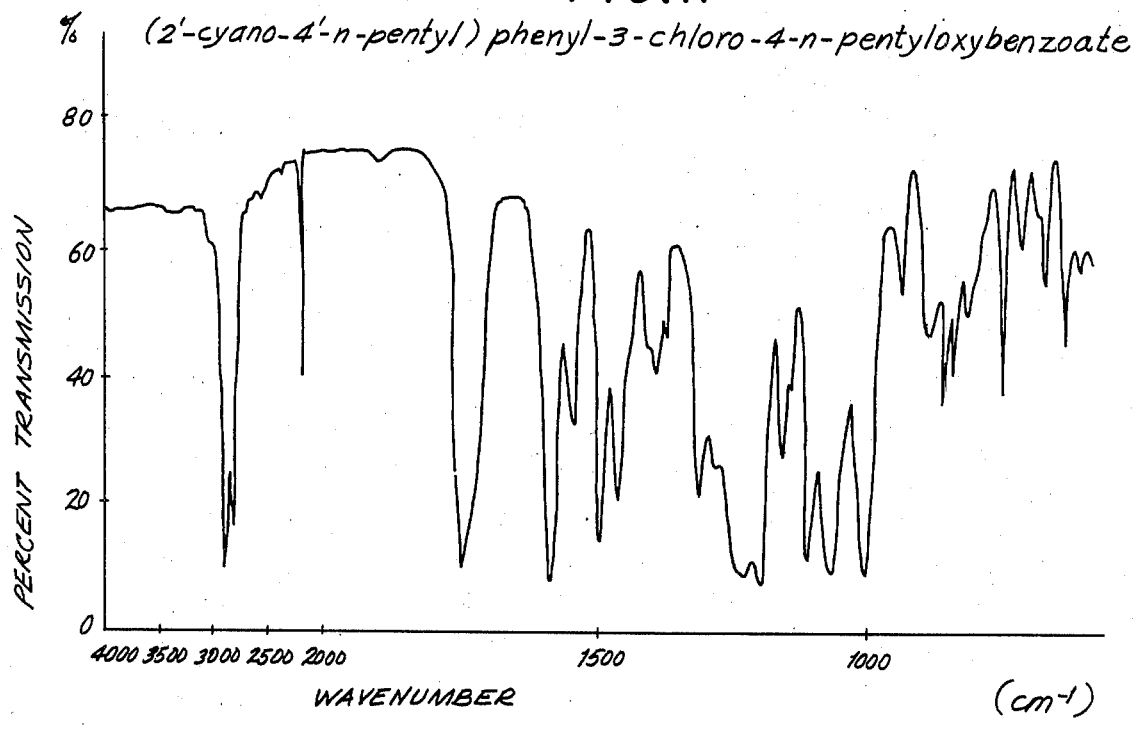
FIG. 11 (2'-cyano-4'-n-pentyl)phenyl-3-chloro-4-n-pentyloxybenzoate
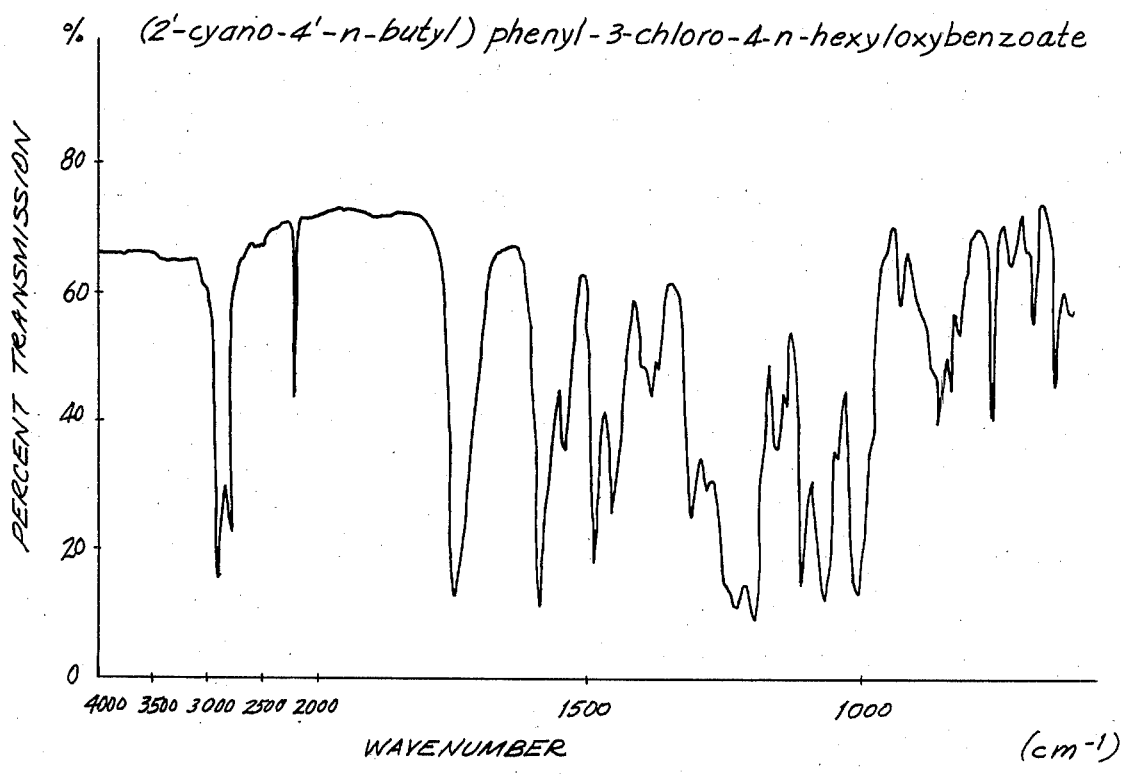
FIG. 12 (2'-cyano-4'-n-butyl)phenyl-3-chloro-4-n-hexyloxybenzoate (2'-cyano-4'-n-hexyl) phenyl-3-chloro-4-n-butyloxybenzoate (2'-cyano-4'-n-butyl) phenyl-3-chloro-4-n-heptyloxybenzoate

(2'-CYANO-4'-N-ALKYL)PHENYL-3-CHLORO-4-N-ALKOXY BENZOATES AND LIQUID CRYSTAL COMPOSITIONS THEREOF

BACKGROUND OF THE INVENTION

This invention relates generally to new ester compounds, liquid crystal compositions including at least one ester compound and to a method of preparing the ester compounds, and particularly to ester compounds which increase the absolute value of the dielectric anisotropy in the high frequency range in a liquid crystal composition suitable for use in a two frequency matrix-addressing drive system.

Liquid crystal display devices are now being widely used for digital displays in electronic devices, such as calculators, timepieces and the like. The method conventionally used for driving the liquid crystal display has progressed from the conventional static drive mode to a multiplex drive mode. The multiplex drive mode now being used is generally referred to as the AC amplitude selective multiplexing method. As long as this method is employed, the number of rows which may be driven is four at the most.

In the generalized AC amplitude selective multiplex method, the ratio $V_{on}/V_{off}$ of the effective voltage $V_{on}$ of the signal applied to the lighted picture cell to that voltage $V_{off}$ applied to the non-lighted picture cell is determined by the number of multiplex lines N. The value of the ratio can be no more than the following formula:

$$V_{on}/V_{off} = \sqrt{\frac{\sqrt{N}+1}{\sqrt{N}-1}} \tag{A}$$

even in the most stable of conditions.

In view of this relationship of the voltage ratio $V_{on}/V_{off}$, the value decreases with an increase in the number of multiplex lines. In other words, as the number N increases, a deterioration in contrast occurs. In presenting a complex character display or a graphical display, it is necessary to increase the number N. Thus, there has been difficulty in applying the conventional generalized AC amplitude selective multiplexing drive method to this type of character or graphic display. Recently, a two-frequency matrix-addressing mode has been found to be effective. The two-frequency mode takes advantage of the low frequency dielectric relaxation phenomenon in a low frequency range and the display is driven by two frequencies. It is expected that this two-frequency matrix-addressing mode can be effective for such complex displays.

The two-frequency matrix-addressing method suffers from the shortcoming that energy consumption is high when the multiplex matrix is addressed. This is due to the fact that high frequencies are applied and the applied voltage increases. This energy consumption may be effectively reduced by making the driving voltage smaller. It is known that the driving voltage V is dependent upon the dielectric anisotropy liquid crystal $\Delta\epsilon$. This relationship may be defined as follows:

$$V \propto \sqrt{\frac{1}{|\Delta\epsilon|}} \tag{B}$$

In other words, as the absolute value $|\Delta\epsilon|$ increases, the value of driving voltage V may be reduced.

The two-frequency matrix-addressing method is characterized in that the voltage ratio between the lighted condition and the non-lighted condition depends not only on the number of rows to be driven, but also the driving voltage and dielectric content as noted in equation (B). In order to take advantage of this relationship, a display device includes a liquid crystal composition wherein the dielectric anisotropy changes from positive to negative depending on this dielectric relaxation as the frequency increases. Such a display device will provide a display without contrast deterioration due to an increment in the number of multiplex lines as it is driven by signals of different frequencies. The first of these signals utilize the positive dielectric anisotrophy of the liquid crystal and the other frequency utilizes the negative dielectric anisotropy of the liquid crystal material.

It is believed that this occurs because the voltage ratio $V_{on}/V_{off}$ of the effective voltage $V_{on}$ of the signal applied to the lighted picture cell to the effective voltage $V_{off}$ of the signal applied to the non-lighted picture cell is dependent not only on the multiplex line number N, but also to the peak value of the voltage of the applied voltage and the dielectric anisotropy of the liquid crystal. Thus, the effective voltage ratio $V_{on}/V_{off}$ can be increased by increasing the peak value of the voltage of the applied signal in the case of the two-frequency method. This permits a display device to provide a display having improved contrast, even when the number of lines N is increased in the two-frequency method. This particular characteristic distinguishes the two-frequency matrix-addressing method from the generalized AC amplitude selective multiplexing method. Specifically, in the latter the voltage ratio $V_{on}/V_{off}$ is determined only by the number of lines N, as shown in formula (A).

Liquid crystal material utilized in the two-frequency matrix-addressing mode has a frequency-dependent dielectric anisotropy which is positive at low frequencies and negative at high frequencies and permits a decrease in driving voltage. This inversion of dielectric anisotropy occurs about the critical frequency $F_c$ at which point the dielectric anisotropy is 0. In order to take advantage of the effects noted above, it is essential that the dielectric anisotropy of the liquid crystal material by highly negative at high frequencies. Specifically, the absolute value of the dielectric anisotropy should be as large as possible.

Accordingly, it is desirable to provide a liquid crystal composition which will have the desired characteristics. Such a liquid crystal compositions may be obtained by mixing a nonliquid crystal materials with a liquid crystal composition, particularly one having a negative dielectric anisotropy at high frequencies. Non-liquid crystal compounds which can be mixed with liquid crystal materials have not been known which will reduce the driving voltage V. Accordingly, it is desirable to provide such a compound, liquid crystal composition including such compound and a method of preparing the compound.

SUMMARY OF THE INVENTION

Generally speaking, in accordance with the invention, an ester compound suitable for use in a liquid crystal composition a liquid crystal composition including such ester compound a method of preparing the ester compound is provided. The new ester compound is a (2'-cyano-4'-alkyl) phenyl-3-chloro-4 alkoxybenzoate which may be represented by the following formula:

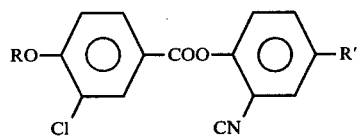

wherein R and R' are selected from the group of straight-chain alkyl groups having from one to eight carbon atoms. The ester compound itself does not have a liquid crystal phase. A small amount of at least one of the ester compounds in accordance with the invention when admixed with a liquid crystal material can provide the increased negative dielectric anisotropy to the liquid crystal material in the high frequency range.

The ester compound is prepared by chlorinating parahydroxybenzoic acid with dichloroamine T, alkolating with a bromalkyl and reacting with thionylchloride to produce the acid chloride of 3-chloro-4-N-alkoxybenzoylchloride. Para-n-alkylphenyl is bromoated and cyanized with cuprous cyanide to produce 2-cyano-4-n-alkylphenol. These two compounds are esterified to yield the desired ester.

The liquid crystal compositions haveing increased negative dielectric anisotropy at high frequencies in accordance with the invention are prepared by mixing at least an effective amount to about 30 weight % of at least one ester compound of the invention with a liquid crystal material to produce the liquid crystal solution compositions of the invention. Liquid crystal materials suitable for use with the ester compounds of the invention are liquid crystal materials having a frequency dependent dielectric anisotropy which is negative at high frequencies. Addition of the ester compounds increases the absolute value of the negative dielectric anisotropy. These liquid crystal compositions are particularly well suited for use in a liquid crystal display device driven in the two-frequency matrix-addressing mode.

Accordingly, it is an object of the invention to provide a new ester compound.

Another object of the invention is to provide an improved liquid crystal composition suitable for use in a two-frequency matrix-addressing method.

A further object of the invention is to provide an improved liquid crystal composition including the new ester compound.

Still another object of the invention is to provide a new ester compound which when mixed with a liquid crystal material increases the negative dielectric anisotropy at high frequencies.

Still a further object of the invention is to provide a method for preparing the new ester compound.

Still other objects and advantages of the invention will in part be obvious and will in part be apparent from the specification.

The invention accordingly comprises the several steps and the relation of one or more of such steps with respect to each of the others, and the composition possessing the features properties, and the relation of constituents which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 5 is graphical representation of the infrared absorption spectrum of 3-chloro-4-n-hexyloxybenzoic acid;

FIG. 6 is a graphical representation of the infrared absorption spectrum of 3-chloro-4-n-hexyloxybenzoylchloride;

FIG. 11 is a graphical representation of the infrared absorption spectrum of (2'-cyano-4'-n-pentyl) phenyl-3-chloro-4-n-pentyloxybenzoate;

FIG. 12 is a graphical representation of the infrared absorption spectrum of (2'-cyano-4'-n-butyl) phenyl-3-chloro-4-n-hexyloxybenzoate;

DESCRIPTION OF THE PREFERRED EMBODIMENTS

The ester compounds in accordance with the invention are (2'-cyano-4'-n-alkyl) phenyl-3-chloro-4-n-alkoxybenzoate which may be represented by the general formula:

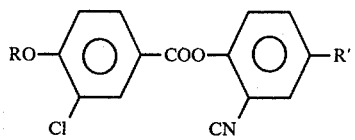

wherein R and R' each is a straight-chain alkyl group having from one to eight carbon atoms. The alkoxybenzoates in accordance with the invention are not themselves liquid crystal materials. However, addition of a small amount of at least one of the alkoxybenzoates to a frequency dependent liquid crystal material effectively yields a liquid crystal composition wherein the absolute value of the negative dielectric anisotropy at high frequency is increased. The frequency dependent liquid crystal materials are those wherein the value of the dielectric anisotropy is positive at low frequencies and is negative at high frequencies. It is believed that the beneficial effect imparted by the alkoxybenzoates of the invention to the liquid crystal composition are due to the linear structure in presence of the two polar groups in the direction of the short axis of the molecule.

The alkoxybenzoates in accordance with the invention may be synthesized by chlorinating with dichloroamine T (N,N-Dichloro-4-methylbenzenesulfonamide) and is then alkoxylated by an alkylbromide. THe benzoylchloride is reacted with thionylchloride to yield 2-chloro-4-alkoxybenzoylchloride. Separately, a para-alkylphenol is bromated and reacted with cuprous cyanide to yield a 2-cyano-4-alkylphenol. The 2-chloro-4-alkoxybenzoylchloride is then condensed with the 2-cyano-4-alkylphenol to yield the (2'-cyano-4'-alkyl) phenyl-3-chloro-4-alkoxybenzoyl.

The synthesis may be illustrated by the following reaction system:

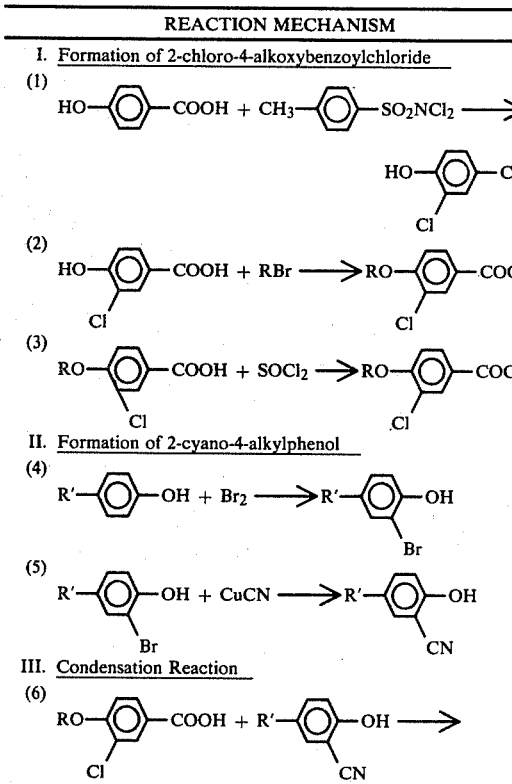

| REACTION MECHANISM |
|---|

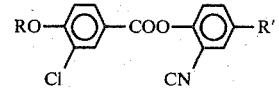

In these formulas, R and R' are each a straight-chain alkyl group having from one to eight carbon atoms as noted above in connection with the general formula for the alkoxybenzoyl.

Preparation of the alkoxybenzoyl in accordance with the invention will be described in detail in the following examples. These examples are intended to be illustrative in are not presented in a limiting sense. All percentages specified are weight percents, based on the total weight of the compositions, unless otherwise indicated.

EXAMPLE 1

Figure 1:
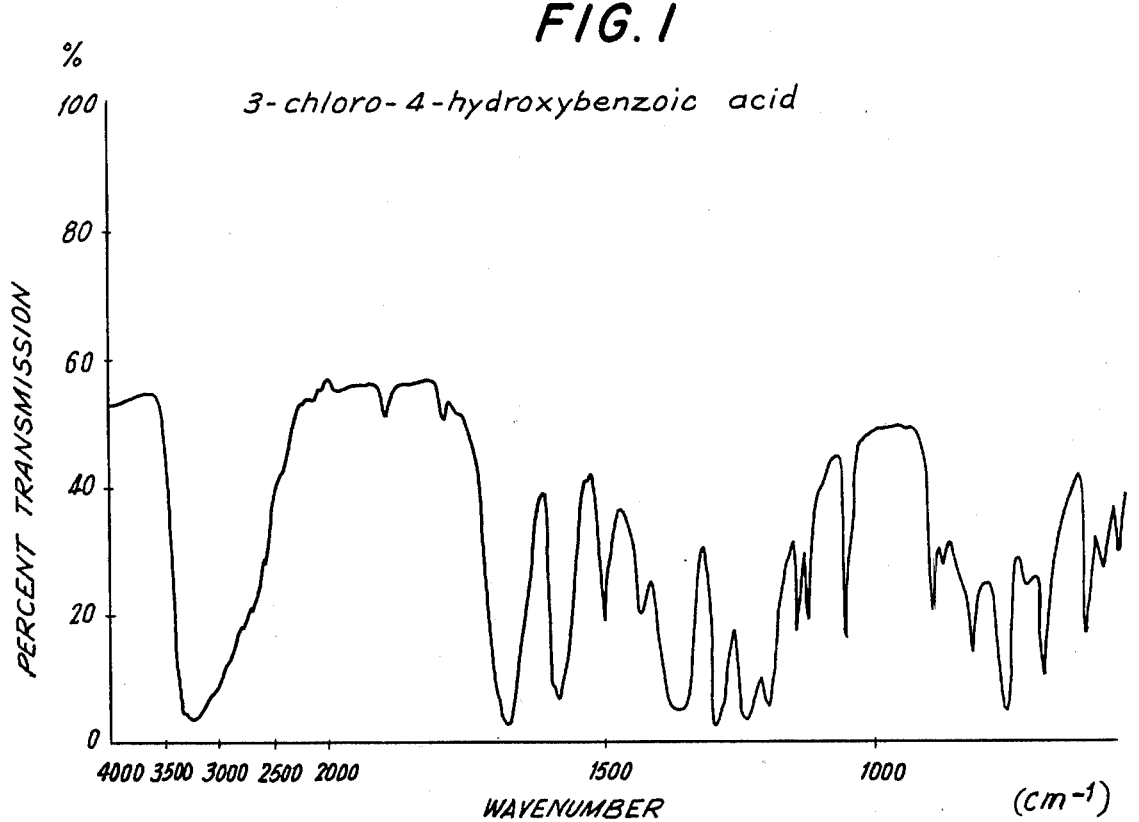
FIG. 1 is a graphical representation of the infrared absorption spectrum of 3-chloro-4-hydroxybenzoic acid.

The ester (2'-cyano-4-n-pentyl) phenyl-3-chloro-4-n-propyloxybenzoate was prepared as follows. 13.8 g (0.1 mol) of a commercial grade para-hydroxybenzoic acid and 12 g (0.05 mol) of dichloroamine T were each dissolved in 100 ml of glacial acetic acid. The two solutions were combined and 0.5 ml of concentrated hydrochloric acid was added and the material was heated to 100° C. for 5 hours. After this time 100 ml of acetic acid was distilled and removed. An appropriate amount of water was added to the remaining liquid thereby producing 16 g of white crystals of 3-chloro-4-hydroxybenzoic acid (hereinafter referred to as material A). The melting point of material A was determined to be 172° C. and the infrared absorption spectrum of material A is shown in FIG. 1.

Figure 2:
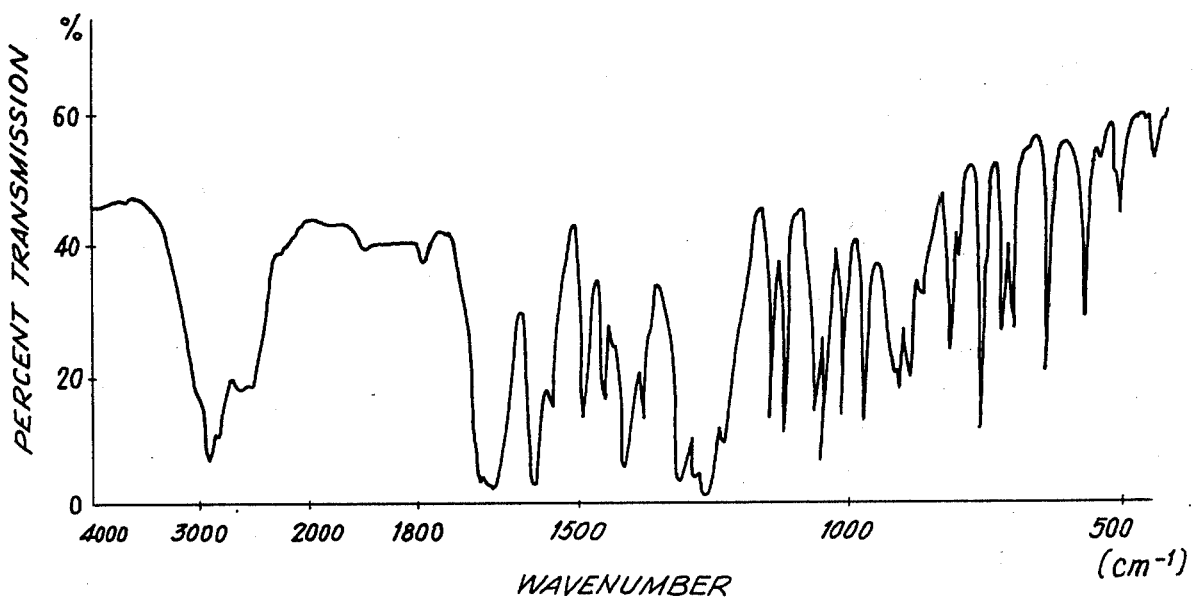
FIG. 2 is a graphical representation of the infrared absorption spectrum of 3-chloro-4-n-propyloxybenzoic acid.

1.73 g (0.01 mol) of material A was dissolved in 50 ml of ethanol. 24.6 g (0.02 mol) of propylbromide was added to the ethanol solution. In a separate vessel 1.15 g (0.02 mol) of potassium hydroxide was dissolved in 5 ml of water and added to the ethanol solution and heated for about 10 hours under refluxing conditions. Following this, 10 ml of a 10% potassium hydroxide solution was added and heated further for 2 hours under refluxing conditions. The material was hydrolyzed and added to a 10% hydrochloric acid solution. The resulting crystals were collected and washed in water yielding 1.2 g of 3-chloro-4-n-propyloxybenzoic acid (hereinafter referred to as material B). The melting point of material B was determined to be 140° C. and the infrared absorption spectrum was obtained as illustrated in FIG. 2.

Figure 3:
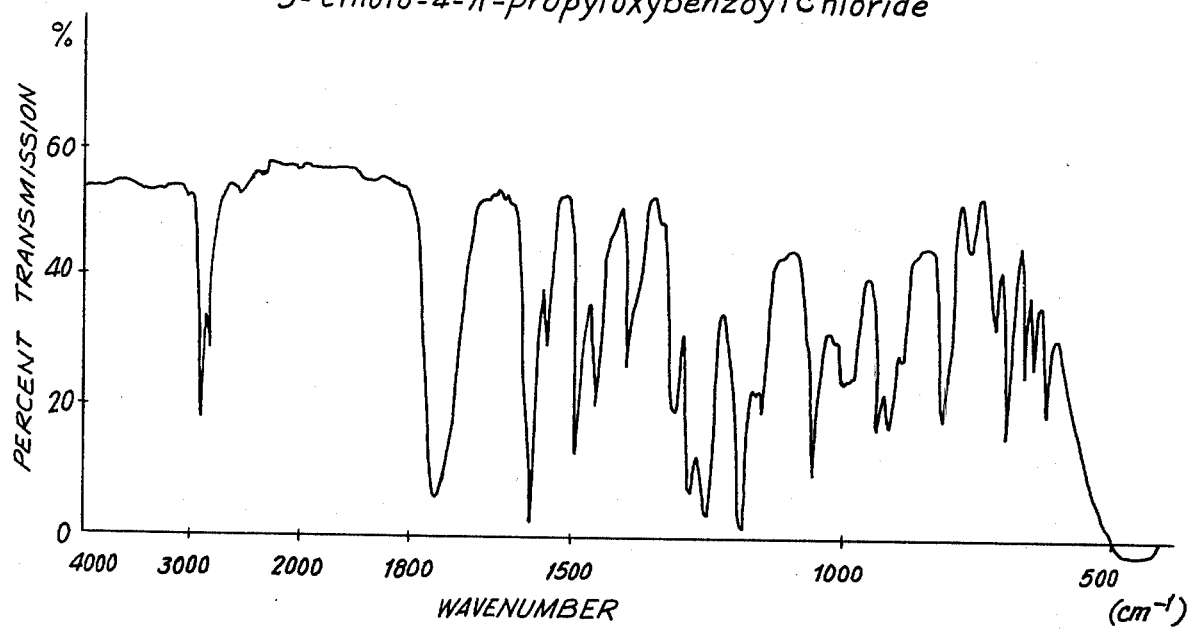
FIG. 3 is a graphical representation of the infrared absorption spectrum of 3-chloro-4-n-propyloxybenzoylchloride.

1.2 g of material B was added to 4 ml of thionylchloride and heated under refluxing conditions for 1 hour. After this time, the remaining thionylchloride was removed and 3-chloro-4-n-propyloxybenzoylchloride (hereinafter referred to as material C) was obtained. The infrared absorption spectrum of the benzoylchloride C is illustrated in FIG. 3. 70 g (0.43 mol) of commercial grade para-n-pentylphenol was dissolved in 200 ml of carbon tetrachloride. 30 ml (0.55 mol) of bromine was added and the mixture was maintained at a temperature of from 40° to 50° C. for 3 hours. After addition of the bromine the solution was maintained under reflux conditions for 4 hours. Carbon tetrachloride was removed by distillation and remaining liquid distilled under reduced pressure to yield 14 mmHg 2-bromo-4-n- pentylphenol (hereinafter referred to as material D) having a boiling point of between 160° and 170° C.

Figure 4:
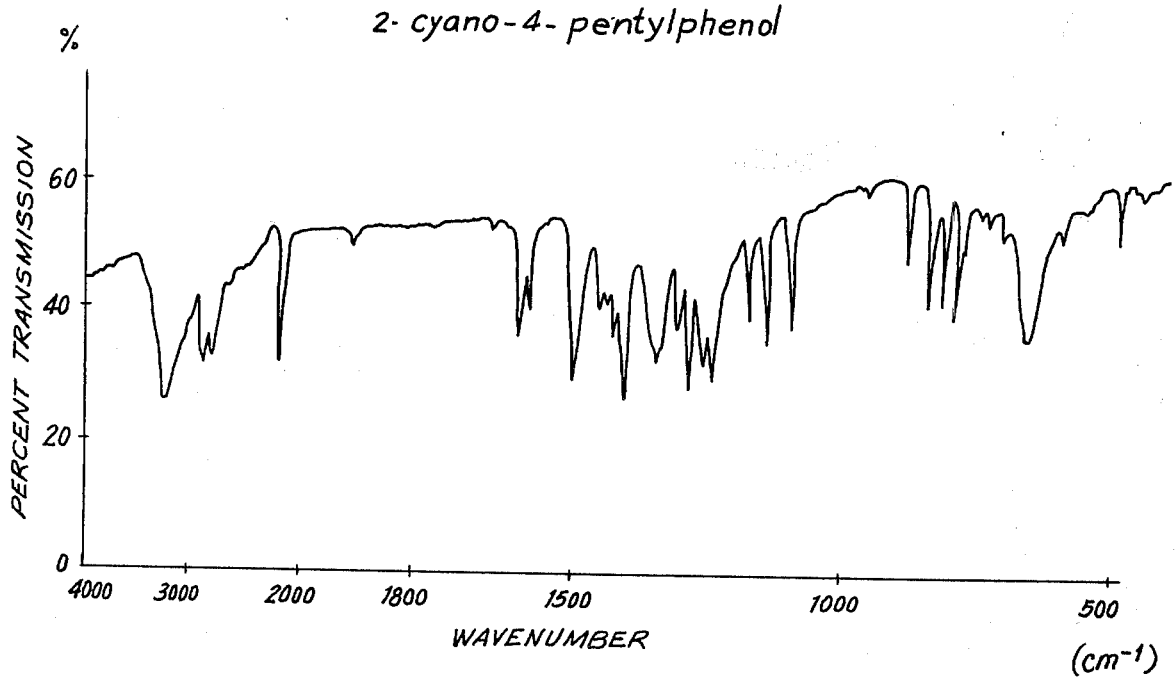
FIG. 4 is a graphical representation of the infrared absorption spectrum of 2-cyano-4-pentylphenol.

31.2 g (0.13 mol) of material D and 13.8 g (0.154 mol) of cuprous cyanide were dissolved in 120 ml of N-methyl-2-pyrrolidone and heated under reflux conditions for 4 hours. Following reflux, the reaction mixture was added to a solution of 56 g of ferric chloride, 21 ml of hydrochloric acid and 100 ml of water and was stirred for 30 minutes at 60° C. A complex salt crystallized, was extracted by ether, washed with 5 N hydrochloric acid and water. The ether was distilled over and removed. The residue was distilled under reduced pressure to yield 2 mmHg 2-cyano-4-n-pentylphenol (hereinafter referred to as material E). Material E had a boiling point of between 130° and 132° C. and a melting point of 78° C. The infrared absorption spectrum of material E is illustrated in FIG. 4.

Figure 9:
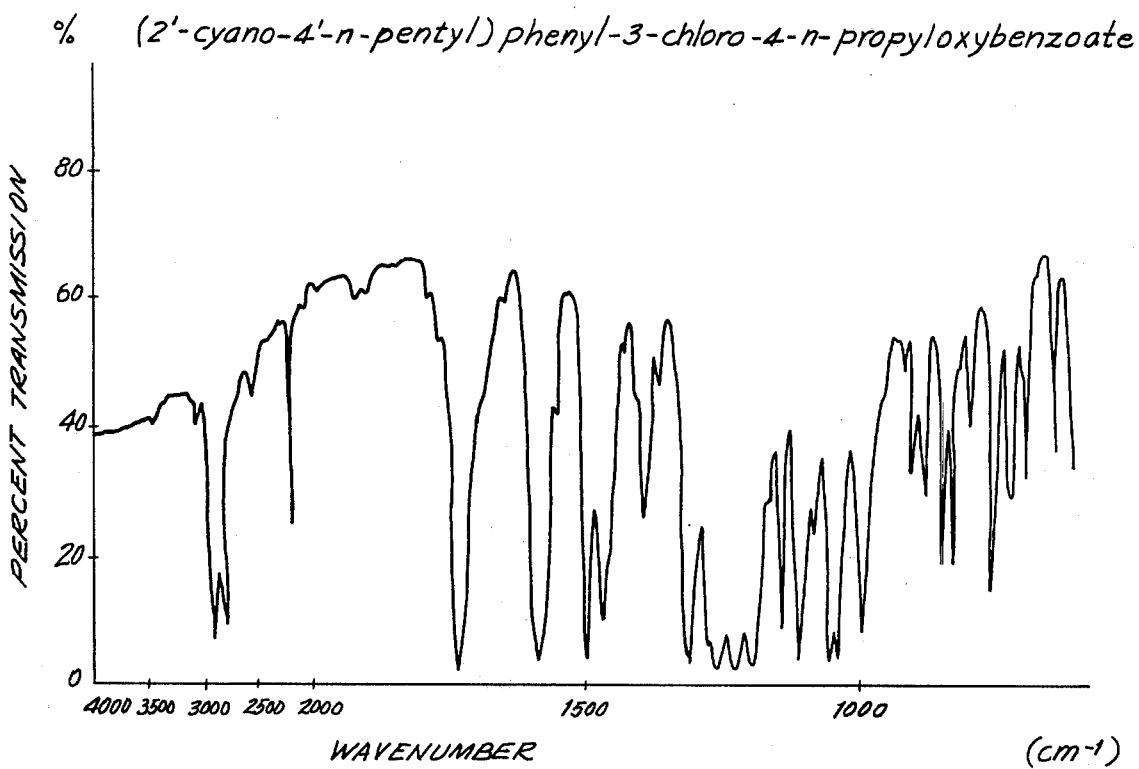
FIG. 9 is a graphical representation of the infrared absorption spectrum of (2'-cyano-4'-n-pentyl) phenyl-3-chloro-4-n-propyloxybenzoate.

0.76 g (0.004 mol) of material E was dissolved in 20 ml of a solution of ethylether and 1 ml of triethylamine and refrigerated. In another vessel, 0.9 g (0.04 mol) of material C was dissolved in 10 ml of ether, mixed with the first vessel with material E, stirred and refluxed on a hot bath for about 1 hour. Following reflux, the solution was hydrolyzed by addition of water and the solids were washed with 5 N hydrochloric acid solution, water, and a 10% caustic soda and water in consecutive order for three times. The ether was then removed by distillation and the residue was recrystallized with ethanol to yield 1.2 g of (2'-cyano-4-n-pentyl) phenol-3-chloro-4-n-propyloxybenzoate. The benzoate had a melting point of 63° C. and an infrared absorption spectrum as illustrated in FIG. 9.

EXAMPLE 2

In accordance with the procedure outlined in Example 1, (2'-cyano-4'-n-propyl) phenyl-3-chloro-4-n-heptyloxybenzoate was prepared.

Utilizing material A (3-chloro-4-n-hydroxybenzoic acid) of Example 1, and n-heptylbromide, 3-chloro-4-heptyloxybenzoylchloride (hereinafter referred to as material F) was prepared in accordance with the procedures of Example 1.

Figure 10:
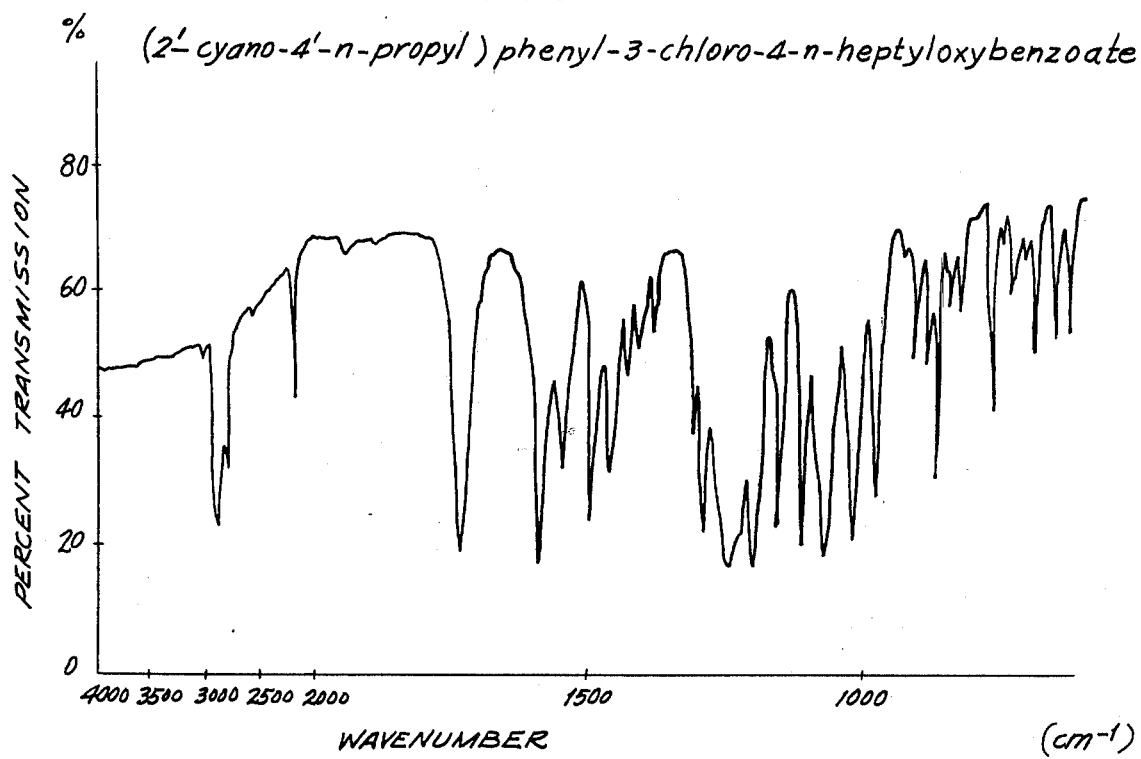
FIG. 10 is a graphical representation of the infrared absorption spectrum of (2'-cyano-4'-n-propyl) phenyl-3-chloro-4-n-heptyloxybenzoate.

Following step (4) of the reaction system, 20.5 g (0.15 mol) of a commercial grade n-propylphenol was dissolved in 100 ml of glacial acetic acid and heated to 40° C. with 24.5 g (0.153 mol) of bromine dissolved in 50 ml of glacial acetic acid. The mixture was stirred and heated at 60° C. for 4 hours. After the reaction was complete, the acetic acid was removed by distillation and the remaining liquid was distilled under reduced pressure to yield 2 mmHg of 2-bromo-4-n-propylphenol having a boiling point of 73° to 76° C. The 2-bromo-4-n-propylphenol was cyanized in accordance with step (5) as in Example 1 to yield 2 mmHg of 2-cyano-4-n-propylphenol (hereinafter referred to as material G) having a boiling point of 110° C. Materials F and G are esterified in accordance with step (6) as in Example 1 to yield the desired (2'-cyano-4'-propyl) phenol-3-chloro-4-n-heptyloxybenzoate. The benzoate had a melting point of 43.5° C. and an infrared absorption spectrum as illustrated in FIG. 10.

EXAMPLE 3

Material E (2-cyano-4-n-penthylphenol) prepared in accordance with the procedure of Example 2 and 3-chloro-4-n-pentyloxybenzoyl chloride synthesized in accordance with phase I of Example 1 are esterified in accordance with phase III to yield (2'-cyano-4'-n-pentyl) phenol-3-chloro-4-n-pentyloxybenzoate. The melting point of the resulting benzoate was 78° C. and had an infrared absorption spectrum as illustrated in FIG. 11.

EXAMPLE 4

The ester compound (2'-cyano-4'-n-butyl) penol-3-chloro-4-n-hexyloxybenzoate in accordance with the invention was prepared as follows. 20.7 g of para-hydroxybenzoic acid and 18 g of dichloroamine T were each dissolved in 150 ml of glacial acetic acid. The two solutions were mixed and 0.75 ml of concentrated hydrochloric acid was added and the mixture heated at 100° C. for 5 hours. At this time, 150 ml of acetic acid was removed by distillation. An appropriate amount of water was added to the liquid residue in order to percipitate 24 g of 3-chloro-4-hydroxybenzoic acid (material A). As noted in Example 1 the infrared absorption spectrum of material A is shown in FIG. 1.

In accordance with step (2) of the reaction system 1.73 g of material A was dissolved in 50 ml of ethanol. 3.3 g of hexylbromide and potassium hydroxide (1.2 g KOH+5 ml $H_2O$) was added and the mixture heated under reflux conditions for 10 hours. Following reflux, a 10% potassium hydroxide solution was added and the mixture refluxed for 2 hours. The mixture was hydrolyzed and then added to dilute hydrochloric acid to promote crystalization. The crystals were washed with water to yield 2 g of 3-chloro-4-n-hexyloxybenzoic acid (hereinafter referred to as material B'). The benzoic acid B' had a melting point of 140° C. and the absorption spectrum is illustrated in FIG. 5.

2 g of the benzoic acid B' and 6 ml of thionylchloride were refluxed until gas was no longer generated. Following the reaction the excess thionylchloride was removed and 3-chloro-4-n-hexyloxybenzoylchloride (hereinafter referred to as material C') was obtained. The infrared absorption spectrum of the benzoylchloride C' is shown in FIG. 6.

In accordance with the procedure of step (4) as described in Example 1, 22.5 g of para-n-butylphenol was dissolved in 100 ml of glacial acetic acid and heated slowly to 40° C. 24.5 g of bromine was added to the solution which was then stirred for 4 hours at 60° C. Following the reaction, the acetic acid was removed by distillation. The remaining liquid was distilled under reduced pressure so that 31.7 g of 2-bromo-4-n-butylphenol (hereinafter referred to as material D') having a boiling point at 85° C. at 1 mmHg was obtained.

Figure 7:
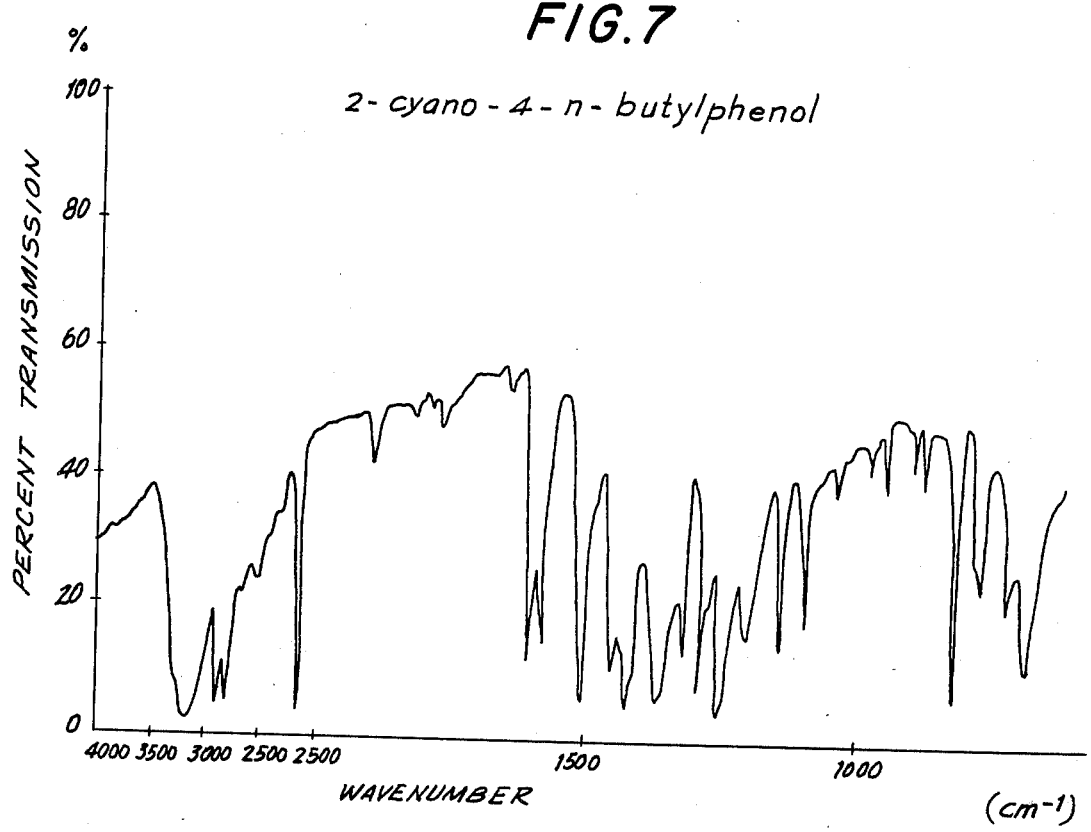
FIG. 7 is a graphical representation of the infrared absorption spectrum of 2-cyano-4-n-butylphenol.
Figure 8:
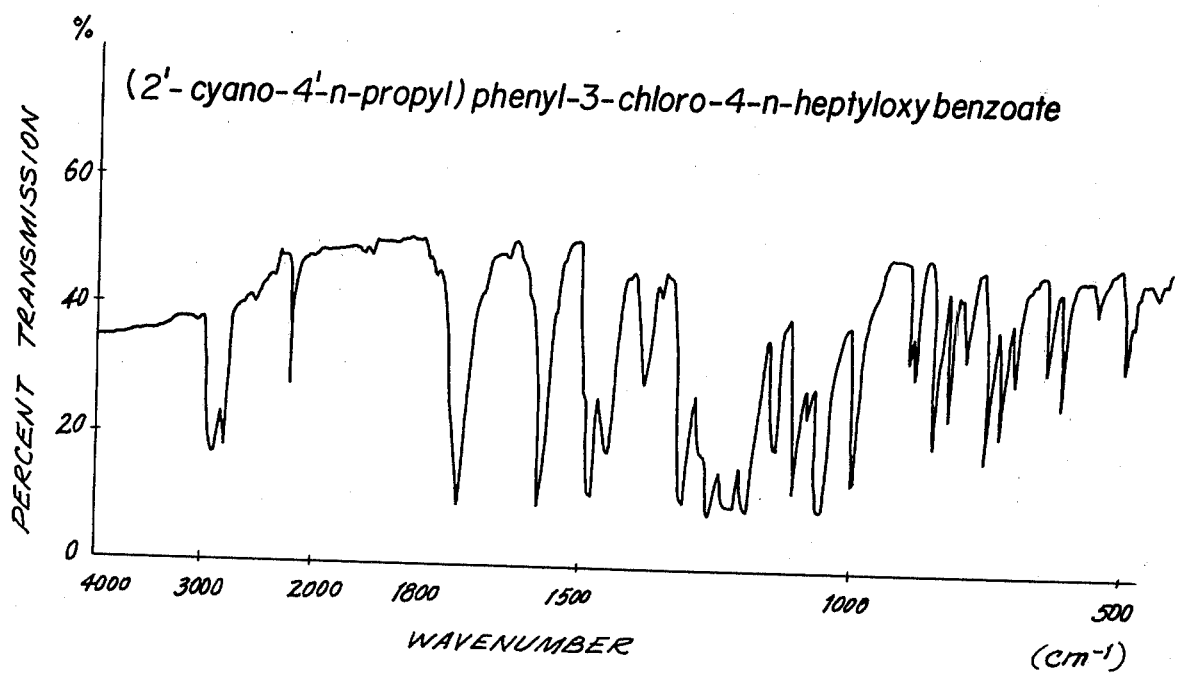
FIG. 8 is a graphical representation of the infrared absorption spectrum of (2'-cyano-4'-n-propyl)phenyl-3-chloro-4-n-heptyloxybenzoate.

As described in Example 1 in connection with step (5) of the reaction system, 16 g of butylphenol D' was dissolved in 70 ml of N-methyl-2-pyrrolidone in the presence of 6.5 g of cuprous cyanide. The suspension was maintained under reflux conditions for 4 hours. The reaction mixture was then cooled to room temperature. In order to decompose the cuprous halogenide and nitrile complex, the liquid mixture was poured into a solution containing 26 g of ferric chloride hydrate dissolved in 100 ml of water and stirred for 30 minutes at 60° to 70° C. This liquid was then poured into 300 ml of cold water and an organic layer was removed by ether extraction, washed with 5 N hydrochloric acid and water followed by distillation to remove the ether. The remaining residue was distilled under reduced pressure yielding 2-cyano-4-n-butylphenol (hereinafter referred to as material E'). The butylphenol E' had a boiling point of 115° C. at 1 mm Hg. The infrared absorption spectrum was as illustrated in FIG. 7.

The condensation reaction of phase III of the reaction mechanism was carried out as follows. 1.8 g of n-butylphenol E' was dissolved in 21 ml of ethyl ether. In a separate vessel 2.7 g of benzoylchloride C' was dissolved in 10 ml of ether 3 ml of pyridine was added to the n-butylphenol as a catalyst and the benzoylchloride was added slowly. Upon completion of addition, the vessel was violently shaken and permitted to float in a water bath. The solution was left to settle for a while and then refluxed for 2 hours. A non-organic salt in the reaction mixture was filtered and removed. The organic layer was washed with hydrochloric acid, caustic and water and the ether was removed by distillation. The residue was recrystallized in hexane in order to obtain the (2'-cyano-4'-n-butyl) phenyl-3-chloro-4-n-hexyloxybenzoate. The benzoate had a melting point of 39.5° C. and an infrared absorption spectrum which is illustrated in FIG. 12.

EXAMPLE 5

In accordance with the procedures of Example 4 and steps (1), (2) and (3) of the reaction mechanism, 3-chloro-4-n-butyloxybenzoylchloride was prepared. In addition, in accordance with steps (4) and (5) of phase II of the reaction mechanism, 2-cyano-4-n-hexylphenyl was prepared.

Figure 13:
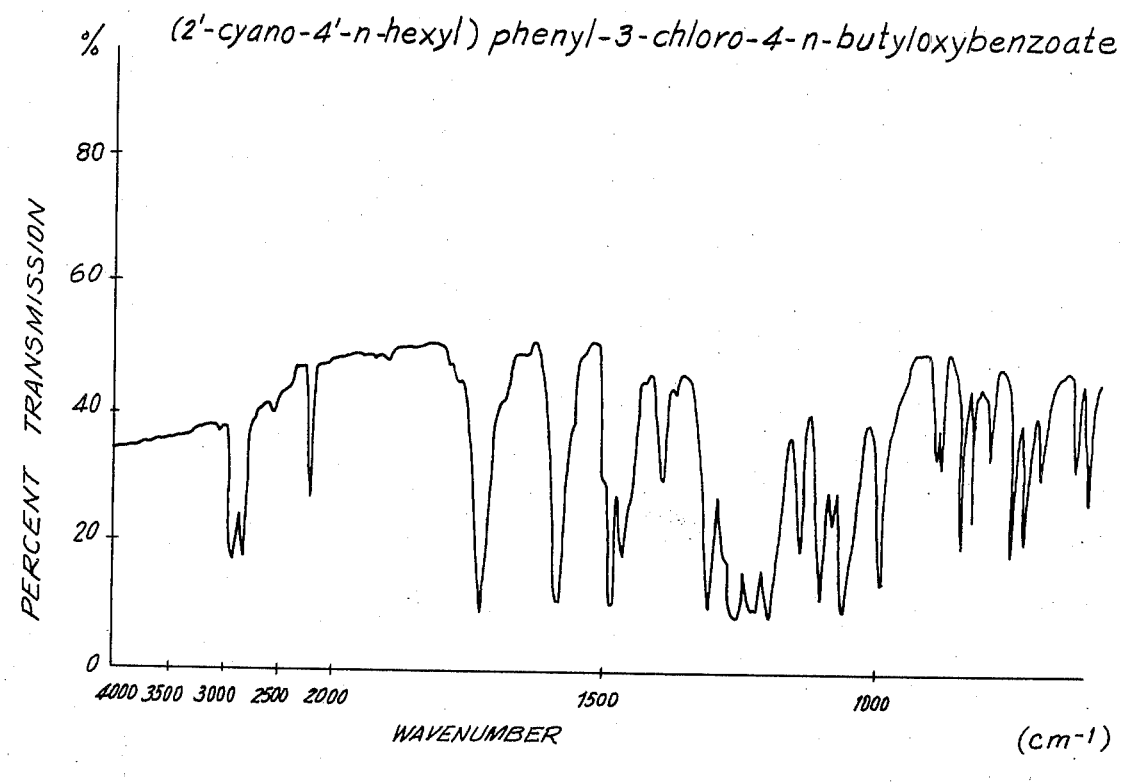
FIG. 13 is a graphical representation of the infrared absorption spectrum of (2'-cyano-4'-n-hexyl) phenyl-3-chloro-4-n-butyloxybenzoate.

The benzoylchloride and phenol were condensed in accordance with phase III of the reaction mechanism to yield ester compound (2'-cyano-4'-n-hexyl) phenyl-3-chloro-4-n-butoxybenzoate. The benzoate had a melting point of 63° C. and an infrared absorption as illustrated in FIG. 13.

EXAMPLE 6

In accordance with the procedures of Example 4 and steps (1), (2) and (3) of the reaction mechanism, 3-chloro-4-n-heptyloxybenzoylchloride was prepared. In addition, in accordance with steps (4) and (5) of phase II of the reaction mechanism, 2-cyano-4-n-heptyloxyphenyl was prepared.

Figure 14:
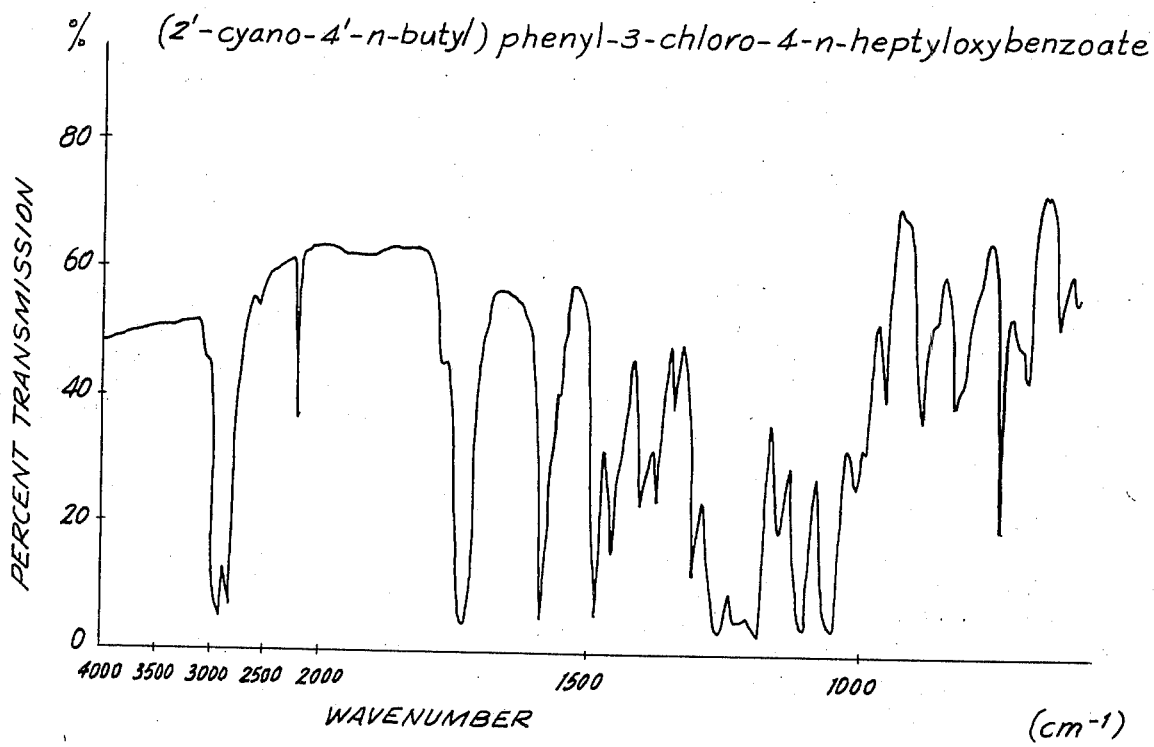
FIG. 14 is a graphical representation of the infrared absorption spectrum of (2'-cyano-4'-n-butyl) phenyl-3-chloro-4-n-heptyloxybenzoate.

The acid chloride and phenyl were condensed in accordance with phase III of the reaction mechanism to yield ester compound (2'-cyano-4'-n-butyl) phenyl-3-chloro-4-n-heptyloxybenzoate. The benzoate had a melting point of 49.5° C. and an infrared absorption as illustrated in FIG. 14.

The structural formulas and melting points of the ester compounds prepared in accordance with the invention in Examples 1-6 are set forth in the following Table I.

TABLE I

| Example | Compound | Melting Point (°C.) | Infrared Spectrum Figure |
|---|---|---|---|
| 1 | C₃H₇O—⟨Cl⟩—COO—⟨CN⟩—C₅H₁₁ | 63 | 9 |
| 2 | C₇H₁₅O—⟨Cl⟩—COO—⟨CN⟩—C₃H₇ | 43.5 | 10 |
| 3 | C₅H₁₁O—⟨Cl⟩—COO—⟨CN⟩—C₅H₁₁ | 78 | 11 |
| 4 | C₆H₁₃O—⟨Cl⟩—COO—⟨CN⟩—C₄H₉ | 39.5 | 12 |
| 5 | C₄H₉O—⟨Cl⟩—COO—⟨CN⟩—C₆H₁₃ | 63 | 13 |
| 6 | C₇H₁₅O—⟨Cl⟩—COO—⟨CN⟩—C₄H₉ | 49.5 | 14 |

EXAMPLE 7

The dielectric anisotropy of a frequency dependent liquid crystal material of para-pentyl-phenyl-2-chloro-4-(parapentylbenzoyloxy) benzoate (hereinafter referred to as liquid crystal compound I) having the structural formula:

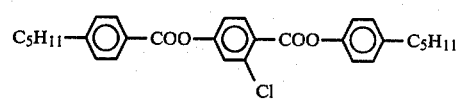

was determined at both a low and high frequency. At a low frequency of 100 Hz, the dielectric anisotropy of liquid crystal compound I had the value of 6. In the high frequency range of 50 KHz, the dielectric anisotropy was −2.

Twenty weight percent of the ester compound prepared in accordance with Example 3, namely (2'-cyano-4'-n-pentyl) phenyl-3-chloro-4-n-pentyloxybenzoate was added to liquid crystal compound I. The dielectric anisotropy of the mixture was measured at both the low frequency of 100 Hz and the high frequency of 50 KHz. The value of the dielectric anisotropy at the low frequency was 6 and at the high frequency was −5.

EXAMPLE 8

The physical characteristics, including the dielectric anisotropy of the ester compound prepared in accordance with the procedures of Example 1 were determined in accordance with the procedures of Example 7. Addition of the (2'-cyano-4'-n-pentyl) phenyl-3-chloro-4-n-propyloxybenzoate provided similar results as observed in accordance with Example 7.

EXAMPLE 9

The physical characteristics, including the dielectric anisotropy of the ester compound prepared in accordance with the procedures of Example 2 were determined in accordance with the procedures of Example 7. Addition of the (2'-cyano-4'-n-propyl) phenyl-3-chloro-4-n-heptyloxybenzoate provided similar results as observed in accordance with Example 7.

EXAMPLE 10

In order to illustrate the effectiveness of the ester compound prepared in accordance with the invention and the beneficial effect on the absolute value of dielectric anisotropy $\Delta\epsilon$ in the high frequency range, the following measurements were made. The dielectric anisotropy of a frequency dependent liquid crystal material para-n-pentylphenyl-2-chloro-4-(p-n-pentylbenzoyloxy) benzoate (Eastman Kodak 11650) was measured. The dielectric anisotropy was measured in the low frequency range (100 Hz) and again in the high frequency range (50 KHz). In addition, the liquid crystal composition including varying weight percents of an ester compound prepared in accordance with Example 7 (2'-cyano-4'-n-butyl) phenyl-3-chloro-4-n-hexyloxybenzoate was admixed in varying amounts of 10, 20 and 30 weight percent with the Kodak 11650 liquid crystal compound. The dielectric anisotropy $\Delta\epsilon$ of these compositions was measured in both the low frequency range (100 Hz) and in the high frequency range (50 KHz). The change in value of the dielectric anisotropy $\Delta\epsilon$ when the benzoate of Example 7 was included is shown in the following TABLE II.

tal substances or with the liquid crystal composition, the ester compound tends to increase the absolute value of the dielectric anisotropy in the high frequency range. As explained earlier, the increase in the absolute value $|\Delta\epsilon|$ of the liquid crystal composition including the ester compound readily overcomes the shortcomings of the liquid crystal materials heretofore utilized in the two-frequency matrix-addressing method. The increase in absolute value of $|\Delta\epsilon|$ aids in orientation of the liquid crystal molecules. The net effect of a display device incorporating such a composition is that the driving voltage may be reduced thereby reducing the energy consumption.

The ester compounds prepared in accordance with the invention are chemically stable so that when mixed with liquid crystal materials, the resulting liquid crystal composition may be utilized in a variety of electro-optical display elements. These elements include the positive type guest-host display elements which now may be driven by reduced driving voltage for reducing the energy consumption. In addition, the ester compounds may be utilized with liquid crystal materials to yield a suitable liquid crystal composition for use in display devices employing the DSM display mode.

The ester compounds prepared in accordance with the invention may be mixed with a large variety of liquid crystal compounds for yielding liquid crystal compositions suitable for use in a display device driven by the two-frequency matrix-addressing mode. The liquid crystal compounds are those liquid crystal compounds which are frequency dependent, namely those which have a positive or 0 frequency dielectric anisotropy and exhibit a dielectric anisotropy inversion with increasing frequency of the applied electric field. Thus, at high frequency ranges the liquid crystal material exhibits a negative dielectric anisotropy. Addition of the ester compound in accordance with the invention which itself does not exhibit liquid crystal properties tends to increase the absolute value of the negative dielectric anisotropy in the high frequency range, thereby improving the properties of a liquid crystal composition including the ester compound.

TABLE II

| | Weight % of Composition (Dielectric Anisotropy) | | | |
|---|---|---|---|---|
| | 100 | 90 | 80 | 70 |
| $C_5H_{11}$—⌬—COO—⌬—COO—⌬—$C_5H_{11}$ | | | | |
| | 0 | 10 | 20 | 30 |
| $C_6H_{13}O$—⌬(Cl)—COO—⌬(CN)—$C_4H_9$ | | | | |
| $\Delta\Sigma L$ (low frequency) | 6 | 6 | 6 | 6 |
| $\Delta\Sigma H$ (high frequency) | −2 | −3.9 | −5.8 | −7.5 |

As noted above, the values of the dielectric anisotropy $\Delta\epsilon L$ and $\Delta\epsilon H$ report the dielectric anisotropy of the liquid crystal composition when the applied frequency is 100 Hz and 50 KHz respectively. As shown, the ester compound prepared in accordance with Example 7 itself does not posses liquid crystal properties. However, addition of the ester compound to a frequency dependent liquid crystal material increases the negative value of the dielectric anisotropy $\Delta\epsilon$ in the high frequency range.

When an ester compound prepared in accordance with the invention is mixed with other non-liquid crys- Generally, the liquid crystal composition prepared in accordance with the invention includes the ester compound of the invention admixed with a frequency dependent-nematic material. Usually, these nematic materials or molecules comprising a linear chain of at least three aromatic groups, preferrably phenylene groups, interconnected through a divalent linking group, such as carboxy group:

wherein the dielectric constant in the longitudinal direction of the liquid crystal molecule begins to diffuse in the lower frequency range, and low viscosity liquid crystal compounds for controlling the viscosity. One of the aromatic groups may be replaced by a cyclohexane ring. The liquid crystal compounds suitable for use in the liquid crystal compositions in accordance with the invention are illustrated in the following TABLE III.

TABLE III

| Liquid crystal compound | Liquid crystal temperature range (°C.) |
| --- | --- |
| n-C$_5$H$_{11}$—⬡—COO—⬡(Cl)—COO—⬡—C$_5$H$_{11}$-n | 39.6 ~ 123 |
| n-C$_7$H$_{15}$—⬡—COO—⬡(Cl)—COO—⬡—C$_5$H$_{11}$-n | 39.5 ~ 101 |
| n-C$_8$H$_{17}$—⬡—COO—⬡(Cl)—COO—⬡—C$_5$H$_{11}$-n | 35.5 ~ 103.5 |
| n-C$_7$H$_{15}$—⬡—COO—⬡(Cl)—⬡—C$_8$H$_{17}$-n | 22 ~ 88 |
| n-C$_8$H$_{17}$—⬡—COO—⬡(Cl)—⬡—C$_8$H$_{17}$-n | 36 ~ 86 |
| C$_2$H$_5$—⟨H⟩—COO—⬡(Cl)—COO—⬡—C$_5$H$_{11}$-n | 50.3 ~ 116.6 |
| n-C$_3$H$_7$—⟨H⟩—COO—⬡(Cl)—COO—⬡—C$_5$H$_{11}$-n | 52 ~ 139.6 |
| n-C$_3$H$_7$—⟨H⟩—COO—⬡(Cl)—COO—⬡—C$_6$H$_{13}$-n | 43.1 ~ 130.7 |
| n-C$_4$H$_9$—⟨H⟩—COO—⬡(Cl)—COO—⬡—C$_8$H$_{13}$-n | 56.3 ~ 126.7 |
| n-C$_5$H$_{11}$—⬡—COO—⬡—COO—⬡(Cl)—CN | 97 ~ 223 |
| n-C$_7$H$_{15}$—⬡—COO—⬡—COO—⬡(Cl)—CN | 85 ~ 196 |
| n-C$_6$H$_{13}$—O—⬡—COO—⬡—COO—⬡(Cl)—CN | 96 ~ 214 |
| n-C$_7$H$_{15}$—⬡—COO—⬡(Cl)—COO—⬡—CN | 69 ~ 160 |
| n-C$_7$H$_{15}$—⬡—COO—⬡(CN)—OOC—⬡—C$_7$H$_{15}$-n | 54 ~ 90 |
| n-C$_4$H$_9$—⟨H⟩—COO—⬡—OC$_2$H$_5$ | 35.5 ~ 74 |
| n-C$_5$H$_{11}$—⟨H⟩—COO—⬡—OC$_3$H$_{11}$-n | 34 ~ 72 |

TABLE III-continued

| Liquid crystal compound | Liquid crystal temperature range (°C.) |
|---|---|
|  | 45 ~ 101 |
|  | 35 |
|  | 29.5 |
|  | 29.5 |

Liquid crystal compositions obtained by mixing liquid crystal compounds of the type illustrated in TABLE III fix the voltage requirement for driving a liquid crystal display including such compositions. The relationship between the driving voltage (VTH) and the dielectric anisotropy ($\Delta\epsilon$) is represented by the relationship $VTH \alpha \sqrt{1/|\Delta\epsilon|}$. At higher frequencies it is desirable to provide the absolute value of $|\Delta\epsilon|$ to be more negative. In other words, the value of $\Delta\epsilon$ should be smaller or more negative. At lower frequencies or no application of voltage, the value of $\Delta\epsilon$ should be positive.

Liquid crystal compositions prepared in accordance with this embodiment of the invention will be illustrated in the following examples. Again, all weight percentages set forth are based on the total weight of the compositions.

EXAMPLE 11

A liquid crystal composition comprising the compound and weight percentages as set forth in TABLE IV was prepared. A liquid crystal display device was filled with this liquid crystal composition in the relationship between the applied frequency and the dielectric anisotropy was examined.

TABLE IV

| Compound | Weight percentage (wt %) | Clearing point (°C.) |
|---|---|---|
|  | 11.8 | |
|  | 11.8 | |
|  | 7.9 | |
|  | 7.9 | |
|  | 5.5 | |
|  | 7.9 | 68.5 |
|  | 15.7 | |
|  | 15.7 | |

TABLE IV-continued

| Compound | Weight percentage (wt %) | Clearing point (°C.) |
|---|---|---|
| 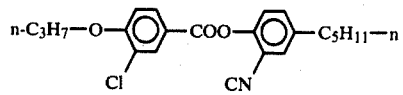 n-$C_3H_7$—O—⟨Cl⟩—COO—⟨CN⟩—$C_5H_{11}$—n | 7.9 | |
| 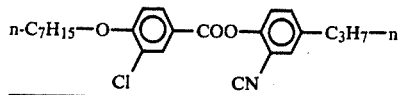 n-$C_7H_{15}$—O—⟨Cl⟩—COO—⟨CN⟩—$C_3H_7$—n | 7.9 | |

Figure 15:
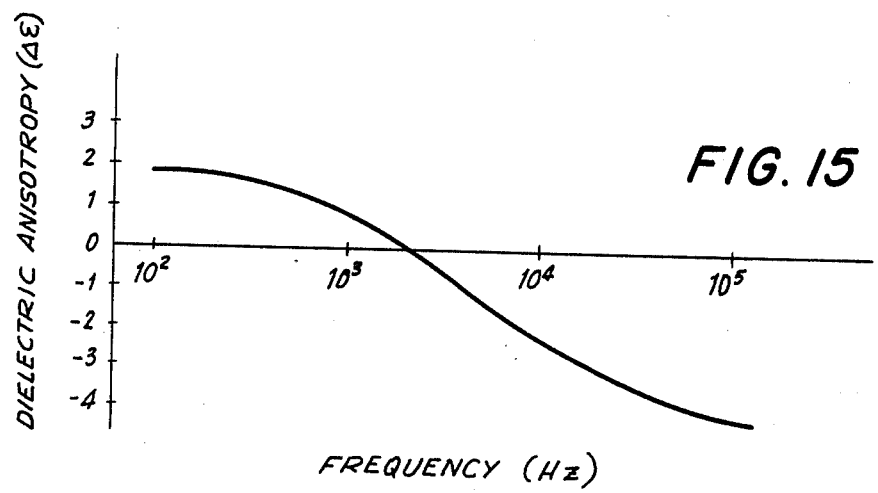
FIG. 15 is a graphical illustration of the relationship between dielectric anisotropy and frequency for the liquid crystal composition of Example 11.

The results of the measurement of the dielectric anisotropy of the display cell at varying frequencies are shown in FIG. 15. It has been found that the dielectric anisotropy is improved at higher frequencies by the addition of the ester compounds prepared in accordance with the earlier embodiments of the invention. The absolute value of the dielectric anisotropy of the conventional liquid crystal material at higher frequency was −2 at the most. As can be seen from FIG. 15, at higher frequencies the negative dielectric anistropy can be increased to a negative value greater than −4.

EXAMPLE 12

Figure 16:
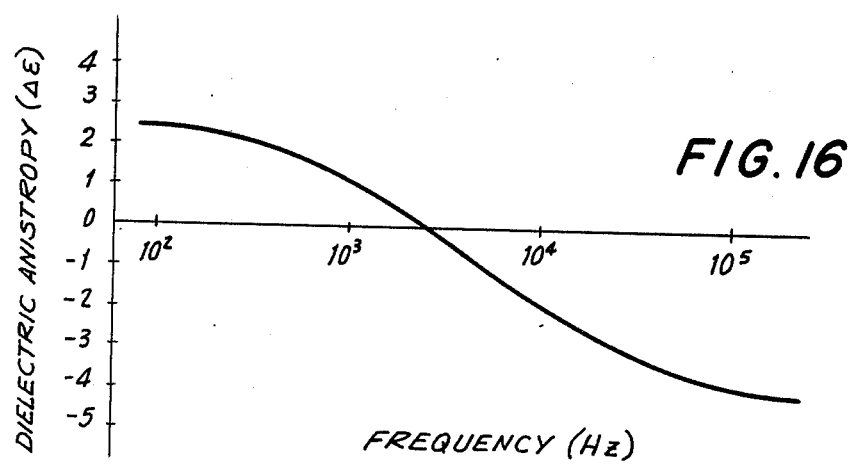
FIG. 16 is a graphical illustration of the relationship between the dielectric anisotropy and frequency for the liquid crystal composition of Example 12.

The procedures of Example 11 were repeated for a liquid crystal composition comprising the compounds listed in TABLE V. Similarly, the results obtained herein were almost the same as for the liquid crystal composition of Example 11. It is noted that the value of the dielectric anisotropy at lower frequencies has been increased as illustrated in FIG. 16.

TABLE V

| Compound | Weight percentage (wt %) | Clearing point (°C.) |
|---|---|---|
| 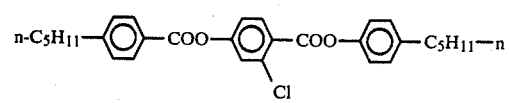 n-$C_5H_{11}$—⟨⟩—COO—⟨Cl⟩—COO—⟨⟩—$C_5H_{11}$—n | 17.5 | |
| 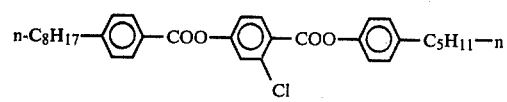 n-$C_8H_{17}$—⟨⟩—COO—⟨Cl⟩—COO—⟨⟩—$C_5H_{11}$—n | 17.5 | |
| 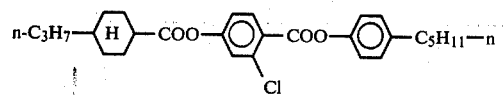 n-$C_3H_7$—⟨H⟩—COO—⟨Cl⟩—COO—⟨⟩—$C_5H_{11}$—n | 6.3 | |
| 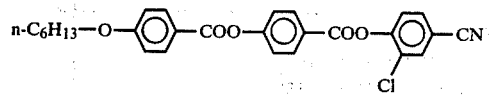 n-$C_6H_{13}$—O—⟨⟩—COO—⟨⟩—COO—⟨Cl⟩—CN | 7.2 | |
| 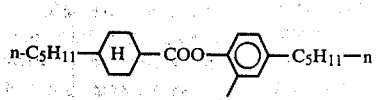 n-$C_5H_{11}$—⟨H⟩—COO—⟨CN⟩—$C_5H_{11}$—n | 10.3 | 70.5 |
| 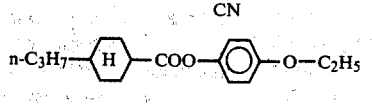 n-$C_3H_7$—⟨H⟩—COO—⟨⟩—O—$C_2H_5$ | 10.3 | |
| 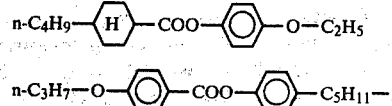 n-$C_4H_9$—⟨H⟩—COO—⟨⟩—O—$C_2H_5$ | 10.3 | |
| 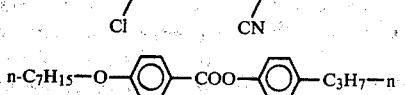 n-$C_3H_7$—O—⟨Cl⟩—COO—⟨CN⟩—$C_5H_{11}$—n | 10.3 | |
| 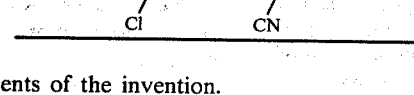 n-$C_7H_{15}$—O—⟨Cl⟩—COO—⟨CN⟩—$C_3H_7$—n | 10.3 | |

EXAMPLE 13

Figure 17:
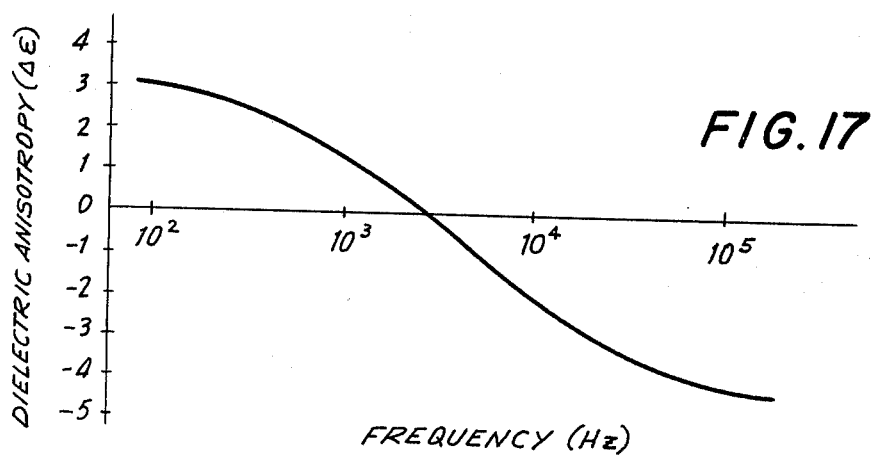
FIG. 17 is a graphical illustration of the relationship between the dielectric anisotropy and frequency for the liquid crystal composition of Example 13.

In accordance with the procedures of Examples 11 and 12, a liquid crystal composition comprising the compounds itemized in TABLE VI was prepared. The results are similar to those obtained in Examples 11 and 12 with a value of the dielectric anisotropy at lower frequencies larger as illustrated in FIG. 17.

TABLE VI

| Compound | Weight percentage (wt %) | Clearing point (°C.) |
|---|---|---|
| n-C₅H₁₁–⌬–COO–⌬(Cl)–COO–⌬–C₅H₁₁-n | 17.5 | |
| n-C₈H₁₇–⌬–COO–⌬(Cl)–COO–⌬–C₈H₁₇-n | 17.5 | |
| n-C₃H₇–⟨H⟩–COO–⌬(Cl)–COO–⌬–C₅H₁₁-n | 11.5 | |
| n-C₇H₁₅–⌬–COO–⌬–COO–⌬(Cl)–CN | 8.0 | |
| n-C₅H₁₁–⟨H⟩–COO–⌬(CN)–C₅H₁₁-n | 10.0 | 78.5 |
| n-C₃H₇–⟨H⟩–COO–⌬–OC₂H₅ | 7.4 | |
| n-C₄H₉–⟨H⟩–COO–⌬–OC₂H₅ | 7.5 | |
| n-C₃H₇–O–⌬(Cl)–COO–⌬(CN)–C₅H₁₁-n | 10.3 | |
| n-C₇H₁₅–O–⌬(Cl)–COO–⌬(CN)–C₃H₇-n | 10.3 | |

When a liquid crystal composition of the type illustrated in Example 11 is driven by a multiplex driving system, 40 volts of driving voltage is sufficient to drive sixty-four rows. However, when using conventional compositions which do not include the ester compounds prepared in accordance with the invention, the number of rows which may be driven by 50 volts or more is at the most thirty-two rows. Accordingly, the liquid crystal compositions prepared in accordance with this embodiment of the invention have excellent characteristics which make the compositions particularly well suited for a display device included in a television set, a character display or other portable electronic device. Significantly, the display devices are particularly well suited for character display devices of the type incorporated in electronic timepieces and calculating devices.

In the liquid crystal composition prepared in accordance with this embodiment of the invention, inclusion of minor amounts of the ester compounds tends to provide the improvement sought in the absolute value of the dielectric anisotropy $|\Delta\epsilon|$. This improvement continues for addition of greater amounts, however, generally speaking between about 5 and 30 weight percent of the ester compound is included. Preferably, between about 15 and about 21 weight percent of the ester compound is included. As shown in the exemplary embodiments of the invention, between about 20 and 21 weight percent is included.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. An ester compound represented by the general formula

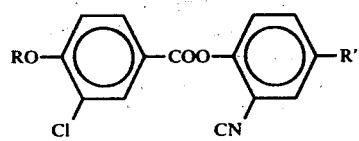

wherein R and R' are selected from the group consisting of straight-chain alkyl groups having from one to eight carbon atoms for defining a (2′-cyano-4′-n-alkyl) phenyl-3-chloro-4-n-alkoxy benzoate.

2. The ester compound of claim 1, wherein R and R′ are selected from the group consisting of straight-chain alkyl groups having from three to seven carbon atoms.

3. The ester compound of claim 1, wherein R is a straight-chain alkyl group having three carbon atoms and R′ is a straight-chain alkyl group having five carbon atoms for defining (2 -cyano-4′-n-pentyl) phenyl-3-chloro-4-n-propyloxybenzoate.

4. The ester compound of claim 1, wherein R is a straight-chain alkyl group having seven carbon atoms and R′ is a straight-chain alkyl group having three carbon atoms for defining (2′-cyano-4′-n-propyl) phenyl-3-chloro-4-n-heptyloxybenzoate.

5. The ester compound of claim 1 wherein R and R′ are straight-chain alkyl groups having five carbon atoms for defining (2′-cyano-4′-n-pentyl) phenyl-3-chloro-4-n-pentyloxybenzoate.

6. The ester compound of claim 1, wherein R is a straight-chain alkyl group having six carbon atoms and R′ is a straight-chain alkyl group having four carbon atoms for defining (2′-cyano-4′-n-butyl) phenyl-3-chloro-4-n-hexyloxybenzoate.

7. The ester compound of claim 1, wherein R is a straight-chain alkyl group having four carbon atoms and R′ is a straight-chain alkyl group having six carbon atoms for defining (2′-cyano-4′-n-hexyl) phenyl-3-chloro-4-n-butyloxybenzoate.

8. The ester compound of claim 1, wherein R is a straight-chain alkyl group having seven carbon atoms and R′ is a straight-chain alkyl group having four carbon atoms for defining (2′-cyano-4′-n-butyl) phenyl-3-chloro-4-n-heptyloxybenzoate.

9. A liquid crystal composition comprising liquid crystal material admixed with at least one (2′-cyano-4′-alkyl) phenyl-3-chloro-4-alkyloxybenzoate represented by the general formula:

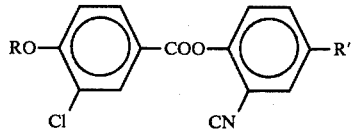

wherein R and R′ are selected from the group consisting of straight-chain alkyl groups having from one to eight carbon atoms.

10. The liquid crystal composition of claim 9, wherein said liquid crystal material includes at least one frequency-dependent liquid crystal compound.

11. The liquid crystal composition of claim 10, wherein said liquid crystal material has a positive dielectric anisotropy in the low frequency range lower than the critical frequency and a negative dielectric anisotropy in the high frequency range above the critical frequency.

12. The liquid crystal composition of claim 11, wherein said benzoate compound is present in at least an amount effective to increase the absolute value of the dielectric anisotropy in the high frequency range.

13. The liquid crystal composition of claim 12, wherein said at least one benzoate is present between the effective amount to about 30 weight percent, based on the total weight of the composition.

14. The liquid crystal composition of claim 12, wherein said at least one benzoate is present in amounts ranging from about 10 to 25 weight percent, based on the total weight of the composition.

15. The liquid crystal composition of claims 9 or 13, wherein said frequency-dependent liquid crystal material includes a nematic liquid crystal material having a linear chain of at least three aromatic groups, interconnected through a divalent linking group.

16. The liquid crystal composition of claim 15, wherein the divalent linking group is a carboxy group.

17. The liquid crystal composition of claim 15, wherein one of the aromatic groups is replaced by a cyclohexane ring.

18. The liquid crystal composition of claim 9, wherein said liquid crystal material includes at least one liquid crystal compound selected from the group consisting of:

| Liquid crystal compound |
|---|

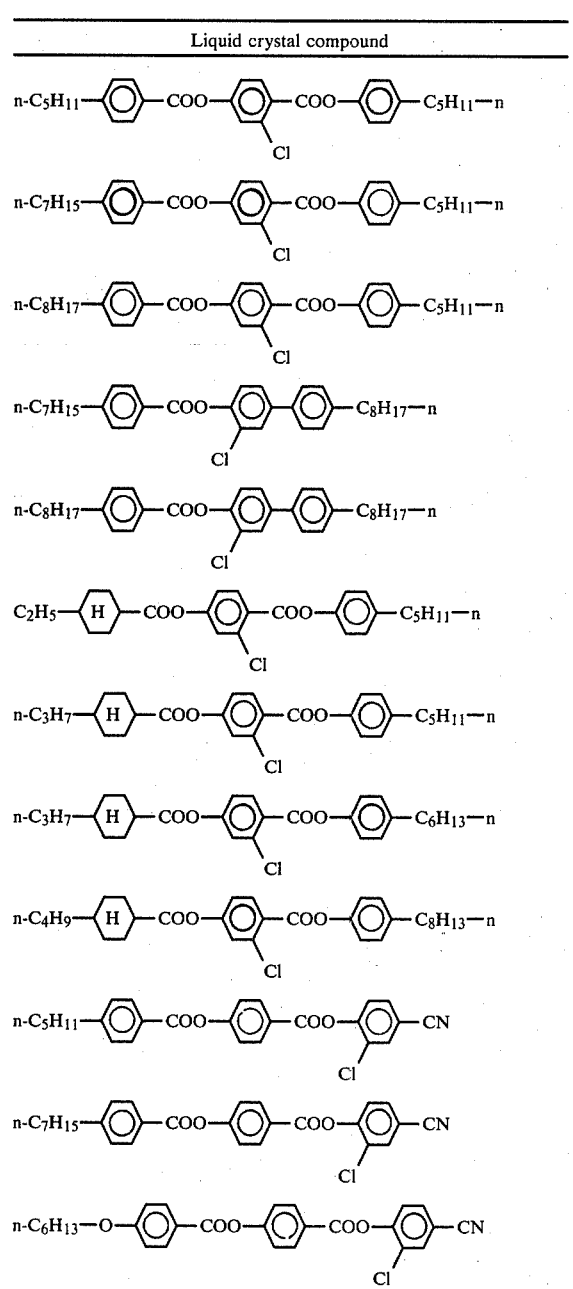

| Liquid crystal compound |
|---|
| n-C7H15—⌬—COO—⌬(Cl)—COO—⌬—CN |
| n-C7H15—⌬—COO—⌬(CN)—OOC—⌬—C7H15-n |
| n-C4H9—⟨H⟩—COO—⌬—OC2H5 |
| n-C5H11—⟨H⟩—COO—⌬—OC3H11-n |
| n-C5H11—⌬—⌬—COO—⌬(CN)—C7H15-n |

| Liquid crystal compound |
|---|
| n-C7H15—⌬—COO—⌬(CN)—C5H11-n |
| n-C3H7—⟨H⟩—COO—⌬(CN)—C5H11-n |
| n-C5H11—⟨H⟩—COO—⌬(CN)—C5H11-n |

19. A liquid crystal composition comprising

| Compound | Weight percentage (wt %) |
|---|---|
| n-C5H11—⌬—COO—⌬(Cl)—COO—⌬—C5H11-n | 11.8 |
| n-C8H17—⌬—COO—⌬(Cl)—COO—⌬—C5H11-n | 11.8 |
| n-C7H15—⌬—⌬—COO—⌬(CN)—C5H11-n | 7.9 |
| n-C3H7—⟨H⟩—COO—⌬(Cl)—COO—⌬—C5H11-n | 7.9 |
| n-C6H13—O—⌬—COO—⌬—COO—⌬(Cl)—CN | 5.5 |
| n-C5H11—⟨H⟩—COO—⌬(CN)—C5H11-n | 7.9 |
| n-C3H7—⟨H⟩—COO—⌬—OC2H5-n | 15.7 |
| n-C4H9—⟨H⟩—COO—⌬—OC2H5-n | 15.7 |
| n-C3H7—O—⌬(Cl)—COO—⌬(CN)—C5H11-n | 7.9 |
| n-C7H15—O—⌬(Cl)—COO—⌬(CN)—C3H7-n | 7.9 |

20. A liquid crystal composition comprising:

| Compound | Weight percentage (wt %) |
|---|---|
| n-C5H11—⌬—COO—⌬(Cl)—COO—⌬—C5H11-n | 17.5 |

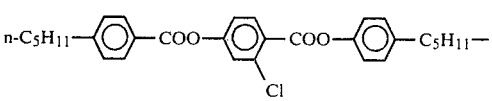

-continued

| Compound | Weight percentage (wt %) |
|---|---|
| 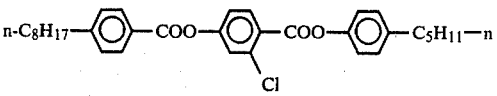 n-C₈H₁₇—⌬—COO—⌬(Cl)—COO—⌬—C₅H₁₁-n | 17.5 |
|  n-C₃H₇—(H)—COO—⌬(Cl)—COO—⌬—C₅H₁₁-n | 6.3 |
|  n-C₆H₁₃—O—⌬—COO—⌬—COO—⌬(Cl)—CN | 7.2 |
| 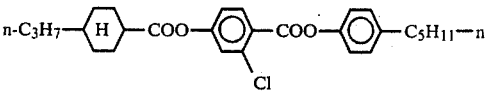 n-C₅H₁₁—(H)—COO—⌬(CN)—C₅H₁₁-n | 10.3 |
|  n-C₃H₇—(H)—COO—⌬—O—C₂H₅ | 10.3 |
|  n-C₄H₉—(H)—COO—⌬—O—C₂H₅ | 10.3 |
| 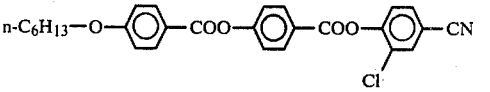 n-C₃H₇—O—⌬(Cl)—COO—⌬(CN)—C₅H₁₁-n | 10.3 |
|  n-C₇H₁₅—O—⌬(Cl)—COO—⌬(CN)—C₃H₇-n | 10.3 |

21. A liquid crystal composition comprising:

| Compound | Weight percentage (wt %) |
|---|---|
|  n-C₅H₁₁—⌬—COO—⌬(Cl)—COO—⌬—C₅H₁₁-n | 17.5 |
| 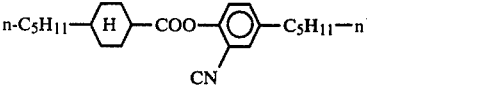 n-C₈H₁₇—⌬—COO—⌬(Cl)—COO—⌬—C₈H₁₇-n | 17.5 |
|  n-C₃H₇—(H)—COO—⌬(Cl)—COO—⌬—C₅H₁₁-n | 11.5 |
| 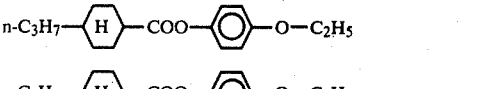 n-C₇H₁₅—⌬—COO—⌬—COO—⌬(Cl)—CN | 8.0 |
|  n-C₅H₁₁—(H)—COO—⌬(CN)—C₅H₁₁-n | 10.0 |
| 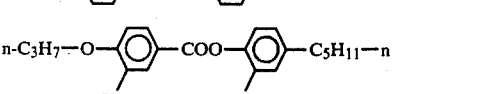 n-C₃H₇—(H)—COO—⌬—OC₂H₅ | 7.4 |
|  n-C₄H₉—(H)—COO—⌬—OC₂H₅ | 7.5 |
| 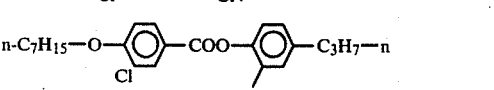 n-C₃H₇—O—⌬(Cl)—COO—⌬(CN)—C₅H₁₁-n | 10.3 |

| Compound | Weight percentage (wt %) |
|---|---|
| n-C₇H₁₅—O—⟨Ph(Cl)⟩—COO—⟨Ph(CN)⟩—C₃H₇-n | 10.3 |

* * * * *